(12) United States Patent
Sun et al.

(10) Patent No.: US 11,746,132 B2
(45) Date of Patent: Sep. 5, 2023

(54) ULTRAMARINE FLUORESCENT PROTEIN, CONSTRUCTION METHOD THEREFOR AND USE THEREOF IN PREPARATION OF PROTEIN SUNSCREEN AGENT

(71) Applicant: Zhejiang Normal University, Jinhua (CN)

(72) Inventors: Meihao Sun, Jinhua (CN); Huihui Wang, Jinhua (CN); Mengmeng Shi, Jinhua (CN); Hongfei Zhou, Jinhua (CN); Jie Liu, Jinhua (CN)

(73) Assignee: Zhejiang Normal University

( * ) Notice: Subject to any disclaimer, the term of this patent is extended or adjusted under 35 U.S.C. 154(b) by 196 days.

(21) Appl. No.: 17/327,313

(22) Filed: May 21, 2021

(65) Prior Publication Data

US 2022/0009975 A1    Jan. 13, 2022

(30) Foreign Application Priority Data

Jul. 7, 2020   (CN) .......................... 202010643785.X (51) Int. Cl.
| | |
|---|---|
| *A61K 8/64* | (2006.01) |
| *C12N 9/02* | (2006.01) |
| *C07K 14/435* | (2006.01) |
| *A61Q 17/04* | (2006.01) |
| *C12N 15/70* | (2006.01) |

(52) U.S. Cl.
CPC .......... *C07K 14/43595* (2013.01); *A61K 8/64* (2013.01); *A61Q 17/04* (2013.01); *C12N 15/70* (2013.01)

(58) Field of Classification Search
CPC .......... A61K 8/64; A61Q 17/04; C12N 15/70
See application file for complete search history.

(56) References Cited

FOREIGN PATENT DOCUMENTS

| | | | |
|---|---|---|---|
| KR | 63556 | * | 6/2015 |
| WO | 020197 | * | 12/2009 |

* cited by examiner

*Primary Examiner* — Maryam Monshipouri
(74) *Attorney, Agent, or Firm* — C. Tumey Law Group PLLC (57) ABSTRACT

An ultramarine fluorescent protein, is a protein selected from (a) and (b) protein: (a) a protein consisting of an amino acid sequence set forth in SEQ ID:NO. 2; (b) a protein derived from (a) by substitution, deletion or addition with one or more amino acids in the amino acid sequence of (a) and having activity of the ultramarine fluorescent protein. The ultramarine fluorescent protein (UFP) has the characteristics of pH-insensitivity and light stability, and its chromophore can absorb long-wavelength ultraviolet (UVA) and release fluorescence at wavelength longer than 400 nm. And the aromatic amino acids residue (with content of 9.2%) can absorb medium wavelength ultraviolet (UVB) and release UVA.

2 Claims, 5 Drawing Sheets

Specification includes a Sequence Listing.

SEQUENCE LISTING

<160> NUMBER OF SEQ ID NOS: 12

<210> SEQ ID NO 1
<211> LENGTH: 759
<212> TYPE: DNA
<213> ORGANISM: Aequorea victoria

<400> SEQUENCE: 1

```
atggctagca tgactggtgg acagcaaatg ggtcgcggat ccgtgagcaa gggcgaggag      60
ctgttcaccg gggtggtgcc catcctggtc gagctggacg gcgacgtaaa cggccacagg     120
ttcagcgtgt ccggcgaggg cgagggcgat gccacctacg gcaagctgac cctgaagctg     180
atctgcacca ccggcaagct gcccgtgccc tggcccaccc tcgtgaccac cctgcagttt     240
ggcgtgctgt gcttcagccg ctaccccgac cacatgaagc agcacgactt cttcaagtcc     300
gccatgcccg aaggctacgt ccaggagcgt accatcttct tcaaggacga cggcaactac     360
aagacccgcg ccgaggtgaa gttcgagggc gacaccctgg tgaaccgcat cgagctgaag     420
ggcatcgact tcaaggagga cggcaacatc ctggggcaca agctggagta caacggcatc     480
agcagcaacg tctatatcac cgccgacaag cagaagaacg gcatcaaggc ccacttcaag     540
atccgccaca acatcgagga cggcagcgtg cagctcgccg accactacca gcagaacacc     600
cccatcggcg acggccccgt gctgctgccc gacaaccact acctgagcgt gcagtccgcc     660
ctgagcaaag accccaacga gaagcgcgat cacatggtcc tgctggagtt cgtgaccgcc     720
gccgggatca ctctcggcat ggacgagctg tacaagtga                             759
```

<210> SEQ ID NO 2
<211> LENGTH: 252
<212> TYPE: PRT
<213> ORGANISM: Artificial Sequence
<220> FEATURE:
<223> OTHER INFORMATION: modified sequence derived from Aequorea victoria

<400> SEQUENCE: 2

```
Met Ala Ser Met Thr Gly Gly Gln Gln Met Gly Arg Gly Ser Val Ser
1               5                   10                  15

Lys Gly Glu Glu Leu Phe Thr Gly Val Val Pro Ile Leu Val Glu Leu
            20                  25                  30

Asp Gly Asp Val Asn Gly His Arg Phe Ser Val Ser Gly Glu Gly Glu
        35                  40                  45

Gly Asp Ala Thr Tyr Gly Lys Leu Thr Leu Lys Leu Ile Cys Thr Thr
    50                  55                  60

Gly Lys Leu Pro Val Pro Trp Pro Thr Leu Val Thr Thr Leu Gln Phe
65                  70                  75                  80

Gly Val Leu Cys Phe Ser Arg Tyr Pro Asp His Met Lys Gln His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
        115                 120                 125

Glu Gly Asp Thr Leu Val Asn Arg Ile Glu Leu Lys Gly Ile Asp Phe
    130                 135                 140

Lys Glu Asp Gly Asn Ile Leu Gly His Lys Leu Glu Tyr Asn Gly Ile
145                 150                 155                 160

Ser Ser Asn Val Tyr Ile Thr Ala Asp Lys Gln Lys Asn Gly Ile Lys
                165                 170                 175
```

```
Ala His Phe Lys Ile Arg His Asn Ile Glu Asp Gly Ser Val Gln Leu
            180                 185                 190

Ala Asp His Tyr Gln Gln Asn Thr Pro Ile Gly Asp Gly Pro Val Leu
            195                 200                 205

Leu Pro Asp Asn His Tyr Leu Ser Val Gln Ser Ala Leu Ser Lys Asp
210                 215                 220

Pro Asn Glu Lys Arg Asp His Met Val Leu Leu Glu Phe Val Thr Ala
225                 230                 235                 240

Ala Gly Ile Thr Leu Gly Met Asp Glu Leu Tyr Lys
            245                 250

<210> SEQ ID NO 3
<211> LENGTH: 26
<212> TYPE: DNA
<213> ORGANISM: Artificial Sequence
<220> FEATURE:
<223> OTHER INFORMATION: F46L-F

<400> SEQUENCE: 3
gaccctgaag ctgatctgca ccaccg                                    26

<210> SEQ ID NO 4
<211> LENGTH: 26
<212> TYPE: DNA
<213> ORGANISM: Artificial Sequence
<220> FEATURE:
<223> OTHER INFORMATION: F46L-R

<400> SEQUENCE: 4
cggtggtgca gatcagcttc agggtc                                    26

<210> SEQ ID NO 5
<211> LENGTH: 30
<212> TYPE: DNA
<213> ORGANISM: Artificial Sequence
<220> FEATURE:
<223> OTHER INFORMATION: T65Q-W66F-F

<400> SEQUENCE: 5
gtgaccaccc tgcagtttgg cgtgcagtgc                                30

<210> SEQ ID NO 6
<211> LENGTH: 36
<212> TYPE: DNA
<213> ORGANISM: Artificial Sequence
<220> FEATURE:
<223> OTHER INFORMATION: T65Q-W66F-R

<400> SEQUENCE: 6
gaagcactgc acgccaaact gcagggtggt cacgag                         36

<210> SEQ ID NO 7
<211> LENGTH: 23
<212> TYPE: DNA
<213> ORGANISM: Artificial Sequence
<220> FEATURE:
<223> OTHER INFORMATION: Q69L-F

<400> SEQUENCE: 7
gtttggcgtg ctgtgcttca gcc                                       23

<210> SEQ ID NO 8
<211> LENGTH: 23
```

```
<212> TYPE: DNA
<213> ORGANISM: Artificial Sequence
<220> FEATURE:
<223> OTHER INFORMATION: Q69L-R

<400> SEQUENCE: 8
ggctgaagca cagcacgcca aac                                              23

<210> SEQ ID NO 9
<211> LENGTH: 40
<212> TYPE: DNA
<213> ORGANISM: Artificial Sequence
<220> FEATURE:
<223> OTHER INFORMATION: Y145G-H148S-F

<400> SEQUENCE: 9
gctggagtac aacggcatca gcagcaacgt ctatatcacc                            40

<210> SEQ ID NO 10
<211> LENGTH: 43
<212> TYPE: DNA
<213> ORGANISM: Artificial Sequence
<220> FEATURE:
<223> OTHER INFORMATION: Y145G-H148S-R

<400> SEQUENCE: 10
ggtgatatag acgttgctgc tgatgccgtt gtactccagc ttg                        43

<210> SEQ ID NO 11
<211> LENGTH: 25
<212> TYPE: DNA
<213> ORGANISM: Artificial Sequence
<220> FEATURE:
<223> OTHER INFORMATION: T203V-F

<400> SEQUENCE: 11
ccactacctg agcgtgcagt ccgcc                                            25

<210> SEQ ID NO 12
<211> LENGTH: 34
<212> TYPE: DNA
<213> ORGANISM: Artificial Sequence
<220> FEATURE:
<223> OTHER INFORMATION: T203V-R

<400> SEQUENCE: 12
gctcagggcg gactgcacgc tcaggtagtg gttg                                  34
```

ULTRAMARINE FLUORESCENT PROTEIN, CONSTRUCTION METHOD THEREFOR AND USE THEREOF IN PREPARATION OF PROTEIN SUNSCREEN AGENT

CROSS REFERENCE TO RELATED APPLICATION

This disclosure claims the priority of Chinese Patent Application NO. 202010643785.X entitled "Ultramarine fluorescent protein, construction method therefor and use thereof in preparation of protein sunscreen agent" filed with China National Intellectual Property Administration on Jul. 7, 2020, which is incorporated herein by reference in its entirety.

TECHNICAL FIELD

The present disclosure belongs to the field of protein construction, in particular relates to an ultramarine fluorescent protein and its construction method and use thereof in preparation of protein sunscreen agent, and further relates to a sunscreen agent containing the ultramarine fluorescent protein.

BACKGROUND ART

In the early 1960s, Shimomura isolated a green fluorescent protein (GFP) from jellyfish for the first time, which is stable at high temperature ($T_m=78°$ C.)[1]. Fluorescent protein (FP) is a kind of protein that can be excited by specific wavelength light to produce fluorescence, and the amino acid residues at positions 65, 66 and 67 forming chromophore[2]. The optical properties of the chromophores are formed by autocatalysis of a tripeptide (residues at 65-67) covalently bound to the central α-helix and buried in a β-barrel structure[3]. The formation of aromatic amino acids and imidazolinone groups at position 66 is closely related to the conjugation of the chromophores and their broad-spectrum properties, the mutation of amino acids at position 66 into aromatic amino acids such as tyrosine, phenylalanine, tryptophan or histidine strongly affects the optical spectrum[4]. A blue fluorescent protein (ultramarine fluorescent protein, UFP1, with an excitation peak at 355 nm and an emission peak at 424 nm) is obtained by the GFP-Phe66 mutation, but its quantum yield is low[5]. An ultramarine fluorescent protein, named Sirius, is obtained after further mutation of UFP1 at positions T65Q, Y145G, H148S and T203V, and its brightness is 80 folds brighter than that of mseCFP-W66F[5]. At present, this protein is mainly used in cell imaging[6], fluorescent probe[7] and so on.

In view of the damage of ultraviolet to the skin[8] and the increasing awareness of ultraviolet protection, people need safer and more efficient sunscreens, and the research and development on new sunscreens has become an important research direction for many researchers. At present, the sunscreens in sunscreen products on the market are mainly chemical absorbents and physical shielding agents, some chemical absorbents will undergo decomposition upon long-time UV exposure, produce free radicals or intermediate products harmful to the human body[9,10], or penetrate into skin due to the small molecular weight[11,12]. The main physical shielding agents are $TiO_2$ and ZnO. With the development of nano-sunscreens, such sunscreens are often prepared into insoluble particles with a diameter of less than 100 nm. However, many studies have reported that these particles are too small and can easily penetrate the skin and enter the blood causing harmful effect to human body[13,14]. Bioengineering sunscreens (such as epidermal growth factor, superoxide dismutase, etc.) are UV protection products developed using bioengineering technology. Their UV protection effect is mainly achieved by regulating the immune function of skin, increasing cell activity, resisting and repairing radiation damage, thereby strengthening the protection effect of chemical sunscreens, and playing an auxiliary and synergistic role. However, there are no related reports about protein used as the major sunscreen agent[8].

Figure 1:
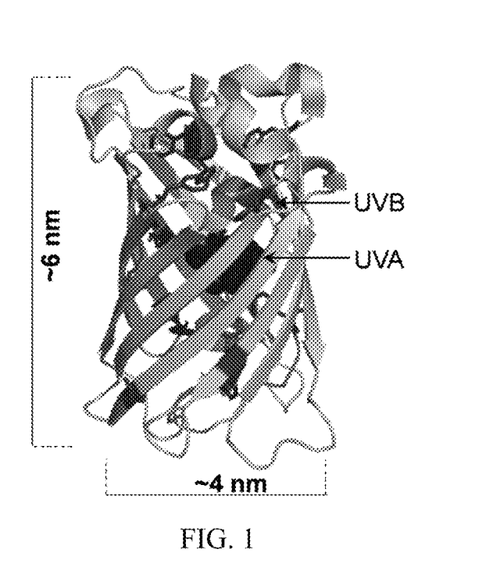

The aromatic amino acids in protein are capable of absorbing UVB, wherein tyrosine has an absorption peak at 275 nm, and the fluorescence released at 305 nm can be absorbed by tryptophan (absorption peak is at 295 nm), which releases fluorescence at about 353 nm. The proportion of aromatic amino acids in UFP is 9.2%, which can absorb a certain amount of UVB and release UVA fluorescence, while the chromophore (absorption peak is at 355 nm) in UFP can absorb the released fluorescence through resonance energy transfer (FIG. 1). Therefore, UFP can theoretically absorb UVA and UVB and release fluorescence with a wavelength longer than 400 nm, which is harmless to the human body. In order to explore sunscreen formulated with proteins, UFP is purified by prokaryotic expression and affinity-purification. In order to improve its purification efficiency, heating treatment combined with an organic solvent extraction method is established to purify the fluorescent proteins. In order to detect its ability to absorb UV light, the anti-ultraviolet ability is analyzed using *Escherichia coli* over expressing the UFP, and its optical characteristics are also analyzed by ultraviolet absorption spectrum and UFP fluorescence spectrum. In order to explore its toxicity to cells, MTT assay is used to analyze the influence of UFP on the growth of TL-OML cells. This study has laid a good foundation for further exploration of the feasibility of UFP as a sunscreen and developmental of safe and broad-spectrum sunscreen products.

SUMMARY OF THE INVENTION

In order to solve the above technical problems, the first objective of the present disclosure is to provide an ultramarine fluorescent protein, the second objective is to provide a gene encoding the above ultramarine fluorescent protein, and the third objective is to provide a construction method for the above ultramarine fluorescent protein, the fourth objective is to provide the use of the above ultramarine fluorescent protein.

Furthermore, the present disclosure provides

An ultramarine fluorescent protein, wherein the ultramarine fluorescent protein is a protein selected from (a) and (b):

(a) a protein consisting of an amino acid sequence set forth in SEQ ID:NO. 2;

(b) a protein derived from (a) by substitution, deletion or addition with one or more amino acids in the amino acid sequence of (a) and having activity of the ultramarine fluorescent protein.

Furthermore, the disclosure also provides a gene encoding the above ultramarine fluorescent protein.

In some embodiments, the nucleotide sequence of the gene is the DNA molecule set forth in SEQ ID: NO. 1.

Furthermore, the disclosure also provides a vector containing the gene.

Furthermore, the disclosure also provides a transformant containing the vector.

Furthermore, the disclosure also provides a method for constructing the above ultramarine fluorescent protein, which comprises the following steps:

1) obtaining DNA molecules by using PCR site-directed mutagenesis: carrying out PCR site-directed mutagenesis by using mutation primers based on F46L, T65Q, W66F, Q69L, Y145G, H148S and T203V sites, with pETCFP-Cl as a template;

2) transforming the obtained DNA molecules into DH5a, and obtaining the gene-mutated UFP after bacteria selection and sequencing;

3) double enzyme digesting pETUFP-Cl, and expression vectors pET-24a and pHND by restriction enzymes BamH I/EcoR I, respectively, and then ligating to construct a pET-24a-UFP vector and a pHND-UFP expression vector for expressing UFP;

4) transforming a mutated plasmid into BL21(DE3), culturing overnight in liquid media, inoculating and further culturing to $OD_{600}$ of 0.5, adding IPTG to induce protein expression for 3 h and collecting the bacteria;

5) suspending the bacteria pellet in the lysis buffer, breaking the bacteria by ultrasonication in an ice bath, centrifugating and collecting a supernatant;

6) heating the supernatant, extracting the supernatant with an organic solvent, and then dialyzing the supernatant to remove impurities, concentrating the protein by low-speed centrifugation in a 3 kD ultrafiltration tube, determining concentration of the UFP protein according to a Bradford technique.

Furthermore, the disclosure also provides a mutation primer sequence in the method, and the sequence of the mutation primers for PCR are as follows:

```
F46L-F:
GACCCTGAAGCTGATCTGCACCACCG

F46L-R:
CGGTGGTGCAGATCAGCTTCAGGGTC

T65Q-W66F-F:
GTGACCACCCTGCAGTTTGGCGTGCA
GTGC

T65Q-W66F-R:
GAAGCACTGCACGCCAAACTGCAGGG
TGGTCACGAG

Q69L-F:
GTTTGGCGTGCTGTGCTTCAGCC

Q69L-R:
GGCTGAAGCACAGCACGCCAAAC

Y145G-H148S-F:
GCTGGAGTACAACGGCATCAGCAGCA
ACGTCTATATCACC

Y145G-H148S-R:
GGTGATATAGACGTTGCTGCTGATGC
CGTTGTACTCCAGCTTG

T203V-F:
CCACTACCTGAGCGTGCAGTCCGCC

T203V-R:
GCTCAGGGCGGACTGCACGCTCAGGT
AGTGGTTG
```

Furthermore, the disclosure also provides the use of the ultramarine fluorescent protein in preparation of protein sunscreen agent.

Furthermore, the disclosure also provides a protein sunscreen agent comprising the ultramarine fluorescent protein.

Due to the adoption of the above-mentioned technical scheme, the ultramarine fluorescent protein (UFP) provided by the present disclosure has the characteristics of pH-insensitivity and light stability, whose chromophore can absorb long-wavelength ultraviolet (UVA) and release fluorescence at wavelength longer than 400 nm. At the same time the aromatic amino acids content is high (9.2%), which can absorb medium wavelength ultraviolet (UVB) and release UVA. UVA can be further absorbed by chromophores through resonance energy transfer, therefore UFP is possible to be developed as a protein sunscreen. UFP is obtained by PCR site-directed mutagenesis, prokaryotic expression, and affinity-purification. A rapid purification method for fluorescent proteins is established by using heating treatment combined with organic solvent extraction. The ability of UFP to absorb ultraviolet is preliminarily analyzed by corresponding spectra and survival experiments after ultraviolet irradiation on E. coli. The toxicity of UFP to cells is analyzed by MTT assay. The results show that the UFP (purity >94.7%) can be purified quickly by heating the supernatant (after the bacteria was broken) at 70° C. for 10 min combined with organic solvent extraction. This method is also applicable to other fluorescent proteins. The ultraviolet absorption spectrum shows that UFP has a certain absorption of ultraviolet rays with a wavelength of 250-400 nm, and the absorption peaks are at 280 nm ($\varepsilon_{max280}$ is $3.27\times10^4$ $M^{-1}\cdot cm^{-1}$) and 365 nm ($\varepsilon_{max365}$ is $1.54\times10^4$ $M^{-1}\cdot cm^{-1}$). The fluorescence spectrum shows that UFP absorbs ultraviolet with a wavelength of 250-400 nm and releases fluorescence longer than 400 nm. The survival experiments of E. coli after ultraviolet irradiation shows that the expression of UFP in E. coli can improve the ability of the strain to resist ultraviolet irradiation. The analysis of MTT assay on toxicity shows that UFP (concentration <5 M) has little effect on growth of TL-OML cell strain. UFP is stable in nature, has an ability to absorb UVB and UVA, does not have toxic effect on cells, and can be used as a broad-spectrum sunscreen agent. The results lay a certain foundation for in-depth study on the use of protein to develop sunscreens.

BRIEF DESCRIPTION OF THE DRAWINGS

FIG. 1 briefly shows the structure of the ultramarine fluorescent protein and its principle of absorbing ultraviolet. The fluorescent chromophore (blue group in the figure) of ultramarine fluorescent protein (UFP) can absorb ultraviolet in UVA, with the maximum absorption peak being at 365 nm, and release fluorescence at a wavelength longer than 400 nm. The aromatic amino acids (red-labeled amino acids) can absorb ultraviolet in UVB, and the released fluorescence lies at 310-350 nm, which can be absorbed by UFP fluorescent chromophores (the distance between them is less than 10 nm, which is within the range of FRET). This protein will have the ability of absorbing UVA and UVB.

DETAILED DESCRIPTION

1 Materials and Methods
1.1 Materials

E. coli DH5α, BL21(DE3) competent cells, and vector pETCFP-Cl containing ECFP (enhanced cyan fluorescent protein) gene were purchased from Yingrun Biotechnologies Inc. (Changsha). pHND vector (containing Hal2 tag)[15] and pET-24a (+) vectors were kept in the laboratory. Restriction endonuclease, DpnI, PCR-related reagents, and T4 DNA ligase, etc. were purchased from Bao Bioengineering Co., Ltd. (Dalian); IPTG, EDTA, ampicillin, kanamycin, yeast extract, and tryptone were purchased from Ox ford LTD (Hampshire, England); DTT, lysozyme, and Pepstatin A were purchased from Amresco Co.; PMSF and EGTA were purchased from BBI life sciences corporation; Ni-NTA His-Bind Super flow Resin was purchased from Novagen Co.; PAP Agarose was purchased from Sigma Co.; ultrafiltration device was purchased from Millipore Co. Other biochemical reagents were all analytically pure and purchased from Chinese companies.

1.2 ECFP Gene Mutation Primers

According to the known gene sequence, primers were designed by using primer premier 5.0 and synthesized by SBS Gene tech Co. Ltd. (Shanghai), the primers used were shown in Table 1.

TABLE 1

List of primers in this study

| Primers | (5'-3')<br>Nucleotide sequence |
|---|---|
| F46L-F | GACCCTGAAGCTGAT<u>CTG</u>CACCACCG |
| F46L-R | CGGTGGTGCAGAT<u>CAG</u>CTTCAGGGTC |
| T65Q-W66F-F | GTGACCACCCTG<u>CAGTTT</u>GGCGTGCAGTGC |
| T65Q-W66F-R | GAAGCACTGCACGCC<u>AAACTG</u>CAGGGTGGTCACGAG |
| Q69L-F | GTTTGGCGTG<u>CTG</u>TGCTTCAGCC |
| Q69L-R | GGCTGAAGCA<u>CAG</u>CACGCCAAAC |
| Y145G-H148S-F | GCTGGAGTACAA<u>CGG</u>CATCAGC<u>AG</u>CAACGTCTATATCACC |
| Y145G-H148S-R | GGTGATATAGACGTT<u>GCT</u>GCTGAT<u>GCC</u>GTTGTACTCCAGCTTG |
| T203V-F | CCACTACCTGAGC<u>GTG</u>CAGTCCGCC |
| T203V-R | GCTCAGGGCGGACTGC<u>AC</u>GCTCAGGTAGTGGTTG |

Note:
Underlined were mutation sites.

1.3 Methods
1.3.1 Site-Directed Mutation of ECFP Gene

The pETCFP-Cl was used as a template, the mutation primers listed in Table 1 were used for PCR site-directed mutation as described in the literature[16]. After the PCR product was digested with Dpn I (final concentration of 1 U/μL) at 37° C. for 3 h, the product was transformed into DH5a by a heat shock method. The positive bacteria were selected and harbored vectors were sequenced to obtain gene of UFP with mutation of F46L, T65Q, W66F, Q69L, Y145G, H148S and T203V.

1.3.2 Construction of UFP Expression Vector

UFP fragment was obtained from the confirmed vector by double enzyme digestion (BamH I, EcoR I). The expression vector pET-24a and pHND were subjected to corresponding double enzyme digestion to obtain a linear vector. UFP fragment and the linear vectors were ligated overnight at 16° C., the ligation product was transformed into BL21(DE3) to obtain pET-24a-UFP and pHND-UFP expression strains.

1.3.3 Analysis of the UV Resistance Ability of E. coli Expressing UFP

A single colony of pET-24a-RFP and pET-24a-UFP were selected and placed into a test tube containing 3 mL of culture medium and cultured overnight at 37° C. and at 220 rpm, the cultures were separately transferred to two flasks containing 100 mL liquid medium for amplifying to $OD_{600}$=0.6, IPTG was added into one flask to a final concentration of 0.5 mM (IPTG was not added into the other flask, which culture was used as a control group), the protein expression was induced for 2 h, the cell pellet was sampled and diluted to an $OD_{600}$ of 0.55~0.65, and then was diluted to 1000 bacteria per mL. 100 μL of diluted bacterial culture was taken and spread on the plate, and then irradiated by ultraviolet (UVB, power 15-20 W, irradiation distance is 56 cm) for 0 s, 10 s, 20 s, 30 s, 40 s, 50 s and 60 s, and left in the incubator overnight at 37° C. Colonies were counted, and survival rates were calculated.

1.3.4 Expression and Purification of Protein

A single colony of the pHND-UFP expression strain was picked and placed in a test tube containing 3 mL of culture medium (with Kanamycin), and cultured overnight at 37° C. and at 220 rpm. The culture was transferred to 500 mL of medium for amplifying the culture. When the $OD_6w$ was 0.4-0.6, IPTG was added to a final concentration of 0.5 mM. After inducing for 3 h under the same condition, the cell pellets were collected for protein purification. The steps of protein purification may be referred to the literature[15,17]. The protein samples obtained by dialysis and purification were concentrated by low-speed centrifuged with a 3 kD ultrafiltration tube. The concentration of Hal2-UFP and UFP protein was determined according to Bradford method[18].

1.3.5 Purification of Fluorescent Protein by Combination of Heating and Organic Solvent Extraction Fluorescent protein has the characteristics of heat resistance and insensitivity to pH and organic solvents. Therefore, to increase the purification efficiency of UFP and improve the feasibility of large-scale production, the purification method to combine heating and organic solvent extraction was explored. First, single colony of pET-24a-UFP expression strain was picked and placed in a test tube containing 3 mL of culture medium and cultured overnight, then the culture was transferred to 500 mL of medium for amplification. The conditions and induction methods were the same as that in step 1.3.4. After induction for 3 h, the cell pellets were collected, 50 mL of lysis buffer (50 mM Hepes, 0.3 M NaCl, 0.1 mg/mL lysozyme) was added and aspirated repeatedly to suspend the cell pellet, the cells were disrupted (ultrasonic or repeated freezing and thawing) after incubation at 4° C. for 30 min, the mixture was centrifuged at 14000×g for 30 min to obtain the supernatant. The supernatant was heated, and the best treatment conditions were explored at different temperatures (55° C., 60° C., 65° C., 70° C. and 75° C.) and different duration time (5 min, 10 min, 20 min and 40 min). The samples were centrifuged at 12000×g for 10 min after heating, the supernatant was taken for protein electrophoresis, the gray level was calculated by using Area Density in the software Vision works, and the optimized temperature and time were selected. The heat-treated samples were further extracted with organic solvent according to the literature[19], and the samples after extraction were dialyzed to remove residual organic solvents and small molecular impurities, and protein concentration were determined according to the method in step 1.3.4.

1.3.6 Analysis of Cytotoxicity

The concentrated proteins were diluted to 50 µM, and the samples were sterilized by filtration with 0.22 µm PVDF. The leukemia cell of TL-OML was treated with four protein concentration set at 0.1, 0.5, 1.0 and 5.0 µM in a 96-well plate, and a blank control was provided. The experimental groups and the blank control were cultured at 5% $CO_2$ and 37° C. for 24 h, 48 h and 72 h, respectively. 10 µL/well of MTT solution was added to the well plates after culturing for different time intervals. After incubating for 3 h, an equal amount of lysis solution was added to crack the cells, and $OD_{595}$ was determined by microplate reader. Each group of data was recorded, the effects of UFP at different concentrations and time intervals on cell growth were plotted, and the influence of UFP on cell viability was analyzed.

1.3.7 Spectrum Analysis

Absorbance spectrums of affinity chromatography purified UFP (74.0 µM) were analyzed using the Scan program of Agilent Cary 4000 UV-Vis-NIR spectrometer from 250 to 550 nm.

The fluorescence spectrum of UFP (4.5 µM) and Hal2-UFP (4.5 µM) excitated by 280 nm were recorded and compared using the Scan program of Agilent Cary Eclipse spectrophotometer. The fluorescence spectrum of UFP with different excitation wavelengths (320 nm, 330 nm, 340 nm, 350 nm, 360 nm, 365 nm and 370 nm) was also analyzed.

2 Results and Analysis

2.1 Results of Protein Purification

Figure 2:
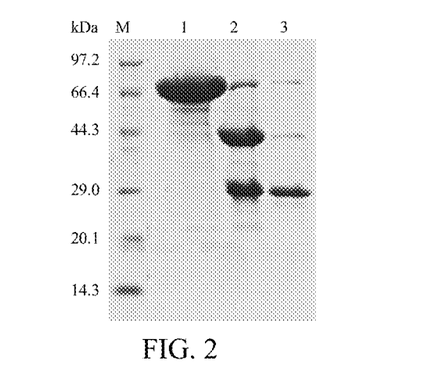
FIG. 2 shows the electrophoresis diagram of results for purification and enzymatic digestion of the Hal2-UFP fusion protein (M. Protein Marker; 1. HAL2-UFP after PAP column purification; 2. HAL2-UFP after enzymatic digestion; 3. HAL2 tag removed after enzymatic digestion).

According to the method of reference[15], the fusion protein Hal2-UFP was purified by a PAP agarose column, and the fusion protein was enzymatic digested by HRV 3C protease, the Hal2 tag in the digested sample was removed by flow through the PAP agarose column again to obtain the final UFP, and the purification results were shown in FIG. 2.

Figure 3:
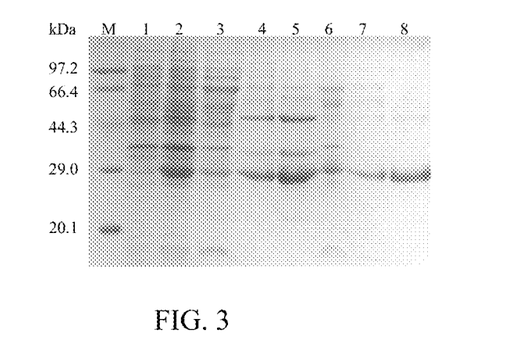
FIG. 3 shows the UFP purification method comparison between the extraction by organic solvents and the combination of organic solvents and heating (M. Protein Marker; 1. E. coli before IPTG induction; 2. E. coli after IPTG induction; 3. Supernatant collected after cell disruption and centrifugation; 4. Sample of ethanol phase after ethanol extraction; 5. Sample of aqueous phase after n-butanol extraction; 6. Supernatant after heating; 7. Sample of ethanol phase after heating followed by ethanol extraction; 8. Sample of aqueous phase after heating followed by n-butanol extraction).
Figure 4:
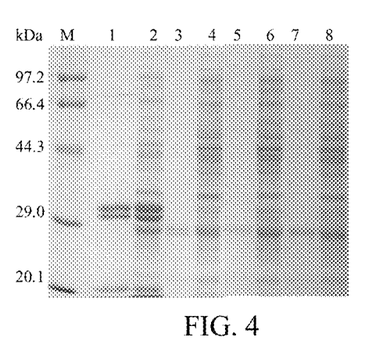
FIG. 4 shows electrophoresis diagrams of different fluorescent proteins purified by heating combined with organic solvent extraction (M. Protein Marker; 1. Red fluorescent protein (RFP) obtained after heating and extraction; 2. supernatant containing RFP after cell disruption and centrifugation; 3. Cyan fluorescent protein (CFP) obtained after heating and extraction; 4. supernatant containing CFP after cell disruption and centrifugation; 5. Yellow fluorescent protein (YFP) obtained after heating and extraction; 6. supernatant containing YFP after cell disruption and centrifugation; 7. Green fluorescent protein (GFP) obtained after heating and extraction; 8. supernatant containing GFP after cell disruption and centrifugation).

Although UFP with a certain purity and content can be obtained by one step affinity chromatography purification, in large-scale practical applications, there are disadvantages such as complex operation, high cost and long cycle. In order to improve the purification efficiency for UFP, the reported method for extracting fluorescent protein with organic solvent[19] was used. Although this method has the advantages of short cycle and simple operation, the purity of the purified sample is limited and further purification is required (FIG. 3, band 5). Fluorescent protein is thermally stable, therefore, the conditions for UFP purification from the supernatant at different temperatures and different times had been explored. The results show that the treatment at 70° C. for 10 min has better effects. The method for purifying high-purity UFP can established by combining heating treatment with organic solvent extraction (FIG. 3, band 8), which is also suitable for the purification of other fluorescent proteins (FIG. 4, Table 2). In addition, the purified sample contains residual organic solvents and other small molecule impurities which need to be removed by dialysis or ultra-filtration.

TABLE 2

Purification of different fluorescent proteins by combination of heating and organic solvent extraction

| Fluorescent protein | Proteins before treatment (mg)[a] | Proteins after purification (mg)[a] | Purity (%)[b] |
|---|---|---|---|
| GFP | 5.56 | 0.18 | 77.1 |
| CFP | 4.94 | 0.15 | 93.8 |
| RFP | 4.23 | 0.34 | 71.8 |
| YFP | 5.80 | 0.21 | 94.9 |
| UFP | 6.20 | 0.25 | 94.7 |

Note:
The value is the average of at least two independent purification.
[a]The total protein concentration is determined according to the Bradford method.
[b]The purity of the target protein is calculated by calculating the gray level of Area Density with Vision works.

2.2 UFP Expression Improves the Anti-Ultraviolet Ability of *E. coli*

Figure 5A:
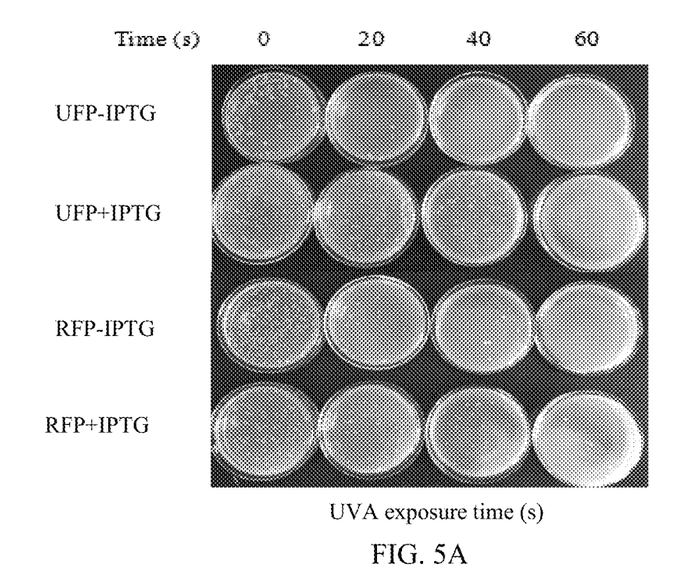
FIG. 5A shows the anti-ultraviolet results of E. coli after UFP expression in vivo. Overnight growth results of survived E. coli after UVA exposure for different time intervals with or without induction of UFP or RFP expression. RFP was used as a control.
Figure 5B:
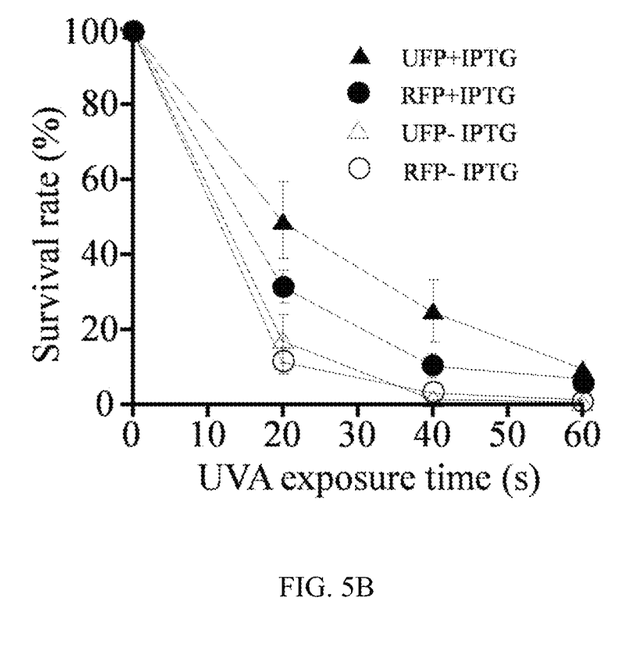
FIG. 5B is a diagram plotting of the data from FIG. 5A.

In order to explore the possible protection effects of high level UFP by absorbing UVB and UVA, UFP was inducing expressed in *E. coli*, and changes of survival ability of *E. coli* under ultraviolet irradiation were analyzed. The results in FIG. 5, shows that when the protein is not expressed in *E. coli*, the survival rate is significantly reduced before 40 seconds of ultraviolet irradiation, and the bacteria does not survive after 60 seconds of irradiation. After the expression of RFP in *E. coli*, the survival rate of *E. coli* is significantly increased possibly resulted from the absorption of UVB by aromatic amino acids in RFP, and the survival rate is 6.2% after irradiating for 60 s. The survival rate is further increased after the expression of UFP in *E. coli*, which indicates that the chromophore of UFP has better UVB absorption ability.

The *E. coli* harboring UFP and RFP genes were divided into two groups, one group was cultured in presence of IPTG for 2 hours, and the other group was cultured in the absence of IPTG for 2 hours. The samples were diluted and cultured on plates, irradiated with UVB (15~20 W, irradiation distance was 56 cm) for different time period. Survival colonies were counted overnight culture. The data were shown as the average f standard deviation (n=3).

2.3 Spectral Analysis of UFP Protein

Figure 6:
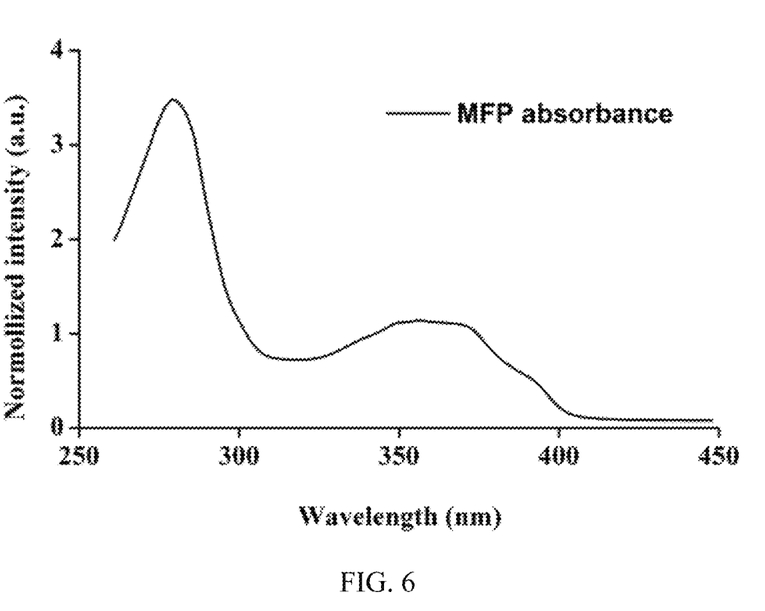
FIG. 6 shows the UV absorption spectrum of UFP.

UFP was purified by affinity chromatography with a PAP agarose column, and its absorption capacity was detected by an ultraviolet spectrophotometer. The results show that UFP has absorption capacity between 250 and 400 nm, and has two absorption peaks at 280 and 360 nm, respectively (FIG. 6). The extinction coefficients corresponding to the two peaks are calculated according to Lambert-Beer law: $A=\varepsilon cl$ (wherein A is the absorbance, $\varepsilon$ is the extinction coefficient, c is the concentration of sample, and l is the optical path). Comparison with some sunscreens whose extinction coefficient have been determined, the UFP has higher extinction coefficient than those of the compared sunscreens (Table 3). This result shows that UFP has the general characteristic of the sunscreen and can absorb UVA and UVB with nice efficacy.

excitation from UFP chromophore has a wavelength greater than 400 nm (FIG. 7B), which has little effect to the skin.

2.4 Analysis of UFP Cytotoxicity

In order to analyze the toxicity of UFP, the MTT assay was used to detect the influence of UFP on the growth of cell strain TL-OML. The results show that there is no significant difference in the cell survival rates treated with different concentrations of UFP samples after 24 h and 48 h treatment (P>0.05). However, at the concentration of 5.0 μM, cell growth is inhibited after 72 h treatment, but no inhibition was observed after 24 h and 48 h treatment.

3 Discussion and Prospective

Fluorescent proteins are proteins that can be excited by a specific wavelength to produce fluorescence, having a molecular mass of about 27 kDa, and forms chromophores by autocatalysis between residues 65-67[21]. Fluorescent protein has a barrel-like structure and has stable properties, and can resist a variety of denaturants such as some proteases, high concentrations of salt (8 M urea), etc., and is pH-independent and thermally stable ($T_m$=78° C.). Based on the in-depth study results from the fluorescent protein crystal structures, fluorescent proteins with different fluorescent properties have been obtained by mutations. UFP is produced from CFP by mutation of seven amino acid residues. UFP chromophore absorption peak is in the range of UVA, and the aromatic amino acids in UFP can absorb UVB and release UVA. Therefore, through resonance energy transfer,

TABLE 3

Extinction coefficient of each sunscreen

| Sunscreen name | Absorption width (nm) | $\lambda_{max}$ (nm) | $\varepsilon_{max}(\times 10^4 M^{-1} \cdot cm^{-1})$ |
|---|---|---|---|
| Benzophenone | 225~290 | 252 | 1.818 |
| Anthranilic acid | 280~370 | 248 ($\lambda_1$) | 0.682 ($\varepsilon_1$) |
|  |  | 336 ($\lambda_2$) | 0.464 ($\varepsilon_2$) |
| Ethylcinnamate | 230~305 | 276 | 2.11 |
| Menthyl o-aminobenzoate | 290~370 | 248.5 ($\lambda_1$) | 0.768 ($\varepsilon_1$) |
|  |  |  | 0.537 ($\varepsilon_2$) |
|  |  | 338 ($\lambda_2$) |  |
| Vanillin | 250~340 | 278 ($\lambda_1$) | 1.04 ($\varepsilon_1$) |
|  |  | 309 ($\lambda_2$) | 1.06 ($\varepsilon_2$) |
| Coumarin | 240~340 | 274 ($\lambda_1$) | 1.10 ($\varepsilon_1$) |
|  |  | 311 ($\lambda_2$) | 0.559 ($\varepsilon_2$) |
| 8-hydroxyquinoline | 270~350 | 240 ($\lambda_1$) | 3.03 ($\varepsilon_1$) |
|  |  | 315 ($\lambda_2$) | 0.262 ($\varepsilon_2$) |
| o-aminobenzoate - benzalkonium bromide quaternary ammonium salt | 270~370 | 247 ($\lambda_1$) | 1.03 ($\varepsilon_1$) |
|  |  | 328 ($\lambda_2$) | 0.526 ($\varepsilon_2$) |
| UFP protein | 240~408 | 280 ($\lambda_1$) | 3.27 ($\varepsilon_1$) |
|  |  | 358 ($\lambda_2$) | 1.54 ($\varepsilon_2$) |

Figure 7A:
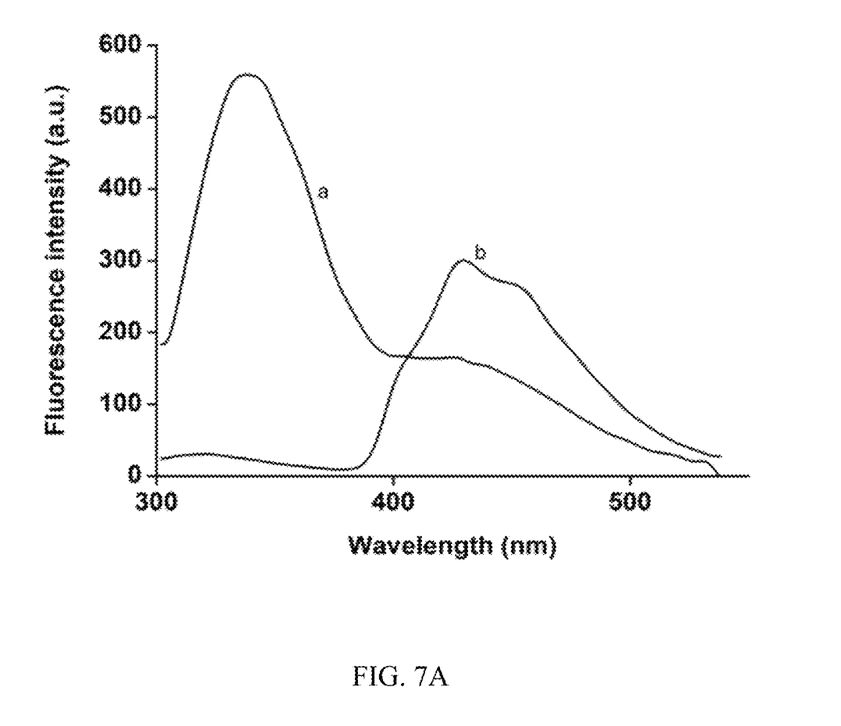
FIG. 7A shows the fluorescence spectrum of Hal2-UFP (a) and UFP (b) at an excitation wavelength of 280 nm.
Figure 7B:
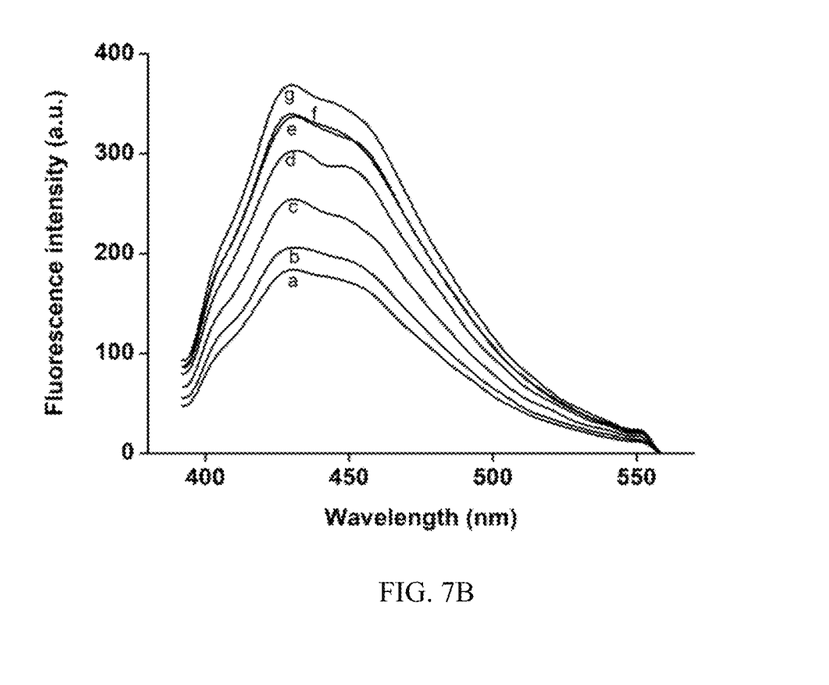
FIG. 7B shows the fluorescence spectrum of UFP at different excitation wavelengths. The a to g are for 370, 320, 330, 340, 360, 350 and 365 nm, respectively.
Figure 8:
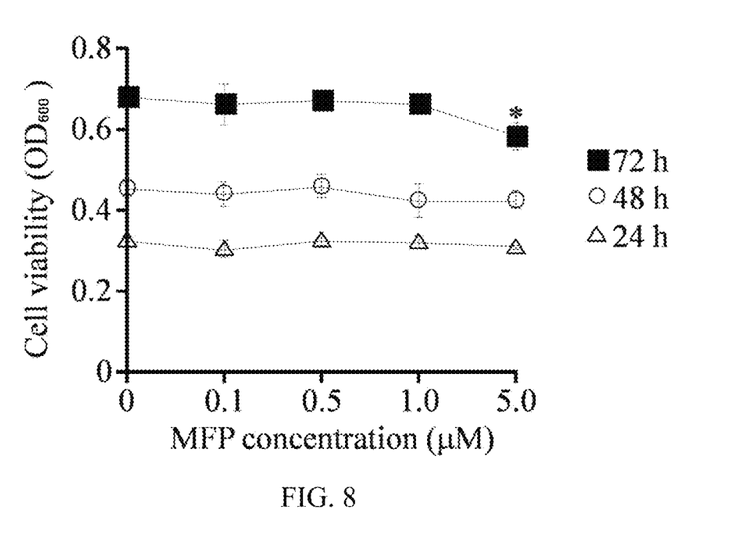
FIG. 8 shows the effect of UFP on cell viability at different concentrations and at different time intervals. The data were shown as the average standard deviation (n=3). Asterisk (*) denotes p<0.05.

The fluorescence characteristics of Hal2-UFP fusion protein and UFP were analyzed by fluorescence spectrophotometer. The results show that when UFP and Hal2-UFP with the same concentration are excited by wavelength of 280 nm, two emission peaks at 325 nm and 436 nm are produced from Hal2-UFP, while only a 435 nm emission peak is produced from UFP (FIG. 7A). It is proven that the fluorescence (300-400 nm) produced from the aromatic amino acid of UFP excited at 280 nm can be absorbed by its own chromophore, and the fluorescence produced from Hal2 in the fusion protein excited at 280 nm cannot be further absorbed by the chromophore because the distance between Hal2 and UFP chromophore is not short enough to meet the FRET requirement[20]. In further analysis of the fluorescence characteristics of UFP, the emission peaks are all about 425 nm when excited with wavelengths of 320-370 nm, indicating that the fluorescence produced by UVA aromatic amino acids and UFP chromophore can absorbs UVA and UVB, and release fluorescence at wavelength longer than 400 nm (FIG. 1). In summary, UFP is used to explore the feasibility of using protein as sunscreen to absorb UVA and UVB.

By ultraviolet absorbance spectrum analysis and fluorescence spectrum analysis, UFP is shown to absorb ultraviolet with wavelength of 250-400 nm, among which ultraviolet from 320 to 400 nm is directly converted into fluorescence of 425 nm. Comparing the fluorescence produced by UFP and by Hal2-UFP under the excitation at 280 nm, it can be shown that ultraviolet rays of 250~320 nm is first converted into fluorescence of about 325 nm, and then converted into fluorescence greater than 400 nm by UFP chromophore. In the energy transforming process described above, the surplus energy is released in the form of heat. Therefore, the effectiveness of UFP on absorbing UVA and UVB is verified. At the same time, the high expression of UFP in *E. coli* increased its resistance to UVB, further indicating the feasibility of UFP working as sunscreen. Currently, fluorescent protein purification methods are diverse, such as organic extraction method[19,22], three-phase separation[23,24], hydrophobic chromatography[25], etc., but when UFP is actually used as sunscreen, the purification efficiency of these methods needs to be improved. UFP can be preliminarily purified initially by heating treatment, and the purity and yield of UFP are significantly improved after combined with organic solvent extraction. To further clarify the safety of UFP, cytotoxicity experiments are carried out by using the MTT assay. The results show that the protein (<5.0 μM) is non-toxic to TL-OML cells for 72 h treatment, which preliminarily shows the safety of UFP. At the same time, the molecular weight of UFP is about 27 kDa, which is stable in nature and will not penetrate the skin. To sum up, based on the current data, UFP can be used as a biological broad-spectrum sunscreen.

This work lays a good foundation for in-depth discussion and study on protein as sunscreen agent. As a kind of sunscreen, the individual indicators still need to be further determined in accordance with the latest "Hygienic Standard for Cosmetics". Study and exploration of potential of UFP or this kind of protein to be used in sunscreens will be continued.

REFERENCES

1. Shimomura O, Johnson F H, Saiga Y. Extraction, purification and properties of aequorin, a bioluminescent protein from the luminous hydromedusan, *Aequorea* [J]. J Cell Comp Physiol, 1962, 59(3):223-239.
2. Ormo M, Cubitt A B, Kallio K, et al. Crystal structure of the *Aequorea victoria* green fluorescent protein [J]. Science, 1996, 273(5280):1392-1395.
3. Patterson G, Day R N, Piston D. Fluorescent protein spectra [J]. J Cell Sci, 2001, 114(Pt 5):837-838.
4. Laurent A D, Assfeld X. Effect of the enhanced cyan fluorescent protein framework on the UV/visible absorption spectra of some chromophores [J]. Interdiscip Sci, 2010, 2(1):38-47.
5. Tomosugi W, Matsuda T, Tani T, et al. An ultramarine fluorescent protein with increased photostability and pH insensitivity [J]. Nat Methods, 2009, 6(5):351-353.
6. Day R N, Davidson M W. The fluorescent protein palette: tools for cellular imaging [J]. Chemical Soc Rev, 2009, 38(10):2887-2921.
7. Matsui A, Umezawa K, Shindo Y, et al. A near-infrared fluorescent calcium probe: a new tool for intracellular multicolour $Ca^{2+}$ imaging [J]. Chem Comm, 2011, 47(37):10407-10409.
8. Huang hongfei, Huang jiong, Shou lu, et al. Research Progress of sunscreen[J]. J Zhejiang Norm Univ (Natural Sciences), 2017, 40(2):206-213.
9. Mturi G J, Martincigh B S. Photostability of the sunscreening agent 4-tert-butyl-4'-methoxydibenzoylmethane (avobenzone) in solvents of different polarity and proticity [J]. J Photoch Photobio A: Chemistry, 2008, 200(2/3):410-420.
10. Karlsson I, Hillerstrom L, Stenfeldt A L, et al. Photodegradation of dibenzoylmethanes: potential cause of photocontact allergy to sunscreens [J]. Chem Res Toxicol, 2009, 22(11):1881-1892.
11. Janjua N R, Kongshoj B, Andersson A M, et al. Sunscreens in human plasma and urine after repeated whole-body topical application [J]. J Eur Acad Dermatol Venereol, 2008, 22(4):456-461.
12. Gonzalez H, Farbrot A, Larko O, et al. Percutaneous absorption of the sunscreen benzophenone-3 after repeated whole-body applications, with and without ultraviolet irradiation [J]. Br J Dermatol, 2006, 154(2):337-340.
13. Gulson B, Mccall M, Korsch M, et al. Small amounts of zinc from zinc oxide particles in sunscreens applied outdoors are absorbed through human skin [J]. Toxico Sci, 2010, 118(1):140-149.
14. Smijs T, Pavel. Titanium dioxide and zinc oxide nanoparticles in sunscreens: focus on their safety and effectiveness [J]. Nanotechnol Sci Appl, 2011, 4(1):95-112.
15. Yang Y, Ma J H, Yang Y L, et al. Yeast 3',5'-bisphosphate nucleotidase: An affinity tag for protein purification [J]. Protein Expr Purif, 2014, 97(2):81-87.
16. Li J, Li C, Xiao W, et al. Site-directed mutagenesis by combination of homologous recombination and DpnI digestion of the plasmid template in *Escherichia coli* [J]. Anal Biochem, 2008, 373(2):389-391.
17. Sun M, Leyh T S. Channeling in sulfate activating complexes [J]. Biochemistry, 2006, 45(38):11304-11311.
18. Bradford M M. A rapid and sensitive method for the quantitation of microgram quantities of protein utilizing the principle of protein-dye binding [J]. Anal Biochem, 1976, 72:248-254.
19. Samarkina O N, Popova A G, Gvozdik E Y, et al. Universal and rapid method for purification of GFP-like proteins by the ethanol extraction [J]. Protein Expr Purif, 2009, 65(1):108-113.
20. Muller S M, Galliardt H, Schneider J, et al. Quantification of Forster resonance energy transfer by monitoring sensitized emission in living plant cells [J]. Front Plant Sci, 2013, 4:413.
21. Craggs T D. Green fluorescent protein: structure, folding and chromophore maturation [J]. Chem Soc Rev, 2009, 38(10):2865-2875.
22. Yakhnin A V, Vinokurov L M, Surin A K, et al. Green fluorescent protein purification by organic extraction [J]. Protein Expr Purif, 1998, 14(3):382-386.
23. Hekmat D, Maslak D, Freiherr Von Roman M, et al. Non-chromatographic preparative purification of enhanced green fluorescent protein [J]. J Biotechnol, 2015, 194:84-90.
24. Jain S, Singh R, Gupta M N. Purification of recombinant green fluorescent protein by three-phase partitioning [J]. J Chromatogr A, 2004, 1035(1):83-86.
25. Mcrae S R, Brown C L, Bushell G R. Rapid purification of EGFP, EYFP, and ECFP with high yield and purity [J]. Protein Expr Purif, 2005, 41(1):121-127.

What is claimed is:

1. An isolated ultramarine fluorescent protein (UFP), wherein the ultramarine fluorescent protein is a protein consisting of the amino acid sequence set forth in SEQ ID NO: 2.

2. The ultramarine fluorescent protein according to claim 1, wherein the nucleotide sequence of a gene encoding the ultramarine fluorescent protein is set forth in SEQ ID NO:1.

* * * * *